United States Patent
Williams et al.

(10) Patent No.: US 9,655,884 B2
(45) Date of Patent: May 23, 2017

(54) ANTIPARASITIC USE OF ISOXAZOLINE COMPOUNDS

(71) Applicant: Intervet Inc., Madison, NJ (US)

(72) Inventors: Heike Williams, Offenbach (DE); Hartmut Zoller, Hocheim (DE); Anja Regina Heckeroth, Stadecken-Elsheim (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/101,430

(22) PCT Filed: Dec. 9, 2014

(86) PCT No.: PCT/EP2014/076959
§ 371 (c)(1),
(2) Date: Jun. 3, 2016

(87) PCT Pub. No.: WO2015/086551
PCT Pub. Date: Jun. 18, 2015

(65) Prior Publication Data
US 2016/0303086 A1    Oct. 20, 2016

(30) Foreign Application Priority Data

Dec. 10, 2013   (EP) .................................. 13196539.4

(51) Int. Cl.
*A61K 31/42*   (2006.01)
*A01N 43/80*   (2006.01)
*C07D 403/10*  (2006.01)
*C07D 471/04*  (2006.01)
*C07D 261/08*  (2006.01)
*A61K 9/00*    (2006.01)

(52) U.S. Cl.
CPC .............. *A61K 31/42* (2013.01); *A01N 43/80* (2013.01); *A61K 9/0053* (2013.01); *C07D 261/08* (2013.01); *C07D 403/10* (2013.01); *C07D 471/04* (2013.01)

(58) Field of Classification Search
CPC ..................................................... C07D 261/08
USPC ......................................................... 514/378
See application file for complete search history.

(56) References Cited

U.S. PATENT DOCUMENTS

2007/0066617 A1    3/2007  Mita

FOREIGN PATENT DOCUMENTS

| WO | EP119256 A1     | 4/2000  |
|----|-----------------|---------|
| WO | WO2005085216    | 9/2005  |
| WO | WO2007079162 A1 | 7/2007  |
| WO | WO2009002809 A2 | 12/2008 |
| WO | WO2009024541    | 2/2009  |
| WO | WO2010070068 A2 | 6/2010  |
| WO | WO200900375 A1  | 7/2010  |
| WO | WO2010079077 A1 | 7/2010  |
| WO | 2013119442 A1   | 8/2013  |
| WO | 2013150052 A1   | 10/2013 |
| WO | WO2013150055 A1 | 10/2013 |

OTHER PUBLICATIONS

Dryden, MW et al, Evaluation of the Ovicidal Activity of Lufenuron and Spinosad on Fleas' Eggs From Treated Dogs., Intern.J.Appl. Res.Vet.Med., 2012, pp. 198-204, 10(3).
Dryden, MW et al, Efficacy of indoxacarb applied to cats against the adult cat flea, Ctenocephalides felis, flea eggs and adult flea emergence., Parasites & Vectors, 2013, pp. 126, 6.
Dryden, MW, Host association, on host longevity and egg production of ctenophalides felis, Veterinarian Parasitology, 1989, 117-122, 34, Elsevier.
International Search Report for application PCTEP2014076959 mailed on Jan. 14, 2015.
Wade, SE et al., Survival and Reproduction of Artificially Fed Cat Fleas, Ctenocephalides Felis Bouché, Journal Med Entomol, 1988, pp. 186-190, 25.

*Primary Examiner* — Raymond Henley, III

(57) ABSTRACT

This invention relates to methods for preventing infestations of animals and their environments with adult fleas by systemic administration of isoxazoline compounds.

11 Claims, No Drawings

ANTIPARASITIC USE OF ISOXAZOLINE COMPOUNDS

CROSS-REFERENCE TO RELATED APPLICATIONS

This application is a national stage entry under 35 U.S.C. §371 of PCT/EP2014/076959, filed on Dec. 9, 2014, which claims priority to EP Application No. EP13196539.4, filed on Dec. 10, 2013, the content of PCT/EP2014/076959 is hereby incorporated by reference in its entirety.

This invention relates to the prophylaxis of parasite infestations in animals.

Isoxazoline compounds are known in the art and compounds from this class are known to possess excellent activity against parasite infestations, such as ticks and fleas.

Isoxazoline compounds and their use as antiparasitics are e.g. described in US patent application US 2007/0066617, and International Patent applications WO 2005/085216, WO 2007/079162, WO 2009/002809, WO 2009/024541, WO 2009/003075, WO 2010/070068 and WO 2010/079077.

One preferred isoxazoline compound is [5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

Flea adulticide (killing) activity of antiparasitics on infested dogs is important, but represents only part of the flea control program needed for effective control of the flea population.

The adult population on the dog represents only approximately 5% of the total flea infestation in a dwelling, while the other 95% of the population consists of juvenile stages of fleas: eggs, larvae and pupae in the dog's home environment [Dryden M W. Host association, on host longevity and egg production of *Ctenocephalides felis*. Vet Parasitol 1989, 34:117-122].

These juvenile (maturing) stages represent a source of re-infestation for the dog as they become adults.

Highly effective control of environmental flea populations has been recorded with topically applied insecticides [Dryden M W, Payne P A, Smith V, Heaney K, Sun F. Efficacy of indoxacarb applied to cats against the adult cat flea, *Ctenocephalides felis*, flea eggs and adult flea emergence. Parasites & Vectors 2013, 6:126] but is not thought to be a feature of systemically administered insecticides [Dryden M W, Payne P A, Smith V, Ritchie L D, Allen L. Evaluation of the Ovicidal Activity of Lufenuron and Spinosad on Fleas' Eggs from Treated Dogs. Intern J Appl Res Vet Med. 2012, 10 (3): 198-204].

The prevention of flea reproduction (development from juvenile stages of fleas to mature (adult) stages by isoxazoline compounds has not been described in prior art.

The isoxazoline compound for use in the current invention can be described by Formula (I):

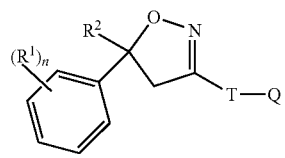

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain CH—CH=CH—CH, N—CH=CH—CH, CH—N=CH—CH, CH—CH=N—CH, or CH—CH=CH—N, HC=HC—CH, CH—CH=CH, CH=CH—N, N—CH=CH;

Q=X—$NR^3R^4$ or a 5-membered N-heteroaryl ring, which is optionally substituted by one or more radicals $Z^A$, $Z^B$ $Z^D$;

X=$CH_2$, CH($CH_3$), CH(CN), CO, CS, $R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methylamino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

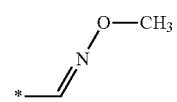

$R^3$-1

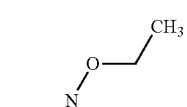

$R^3$-2

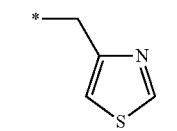

$R^3$-3

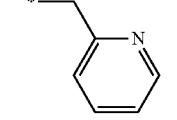

$R^3$-4

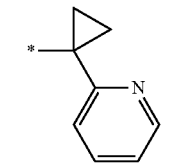

$R^3$-5

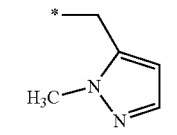

$R^3$-6

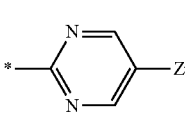

$R^3$-7

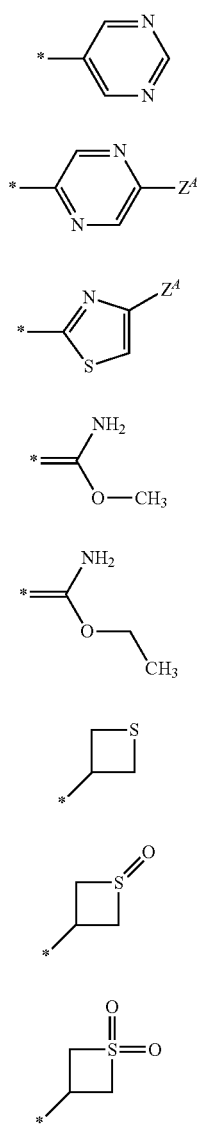

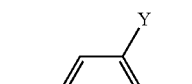
T-1

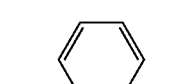
T-2

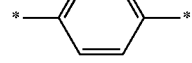
T-3

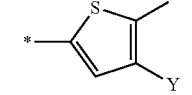
T-4

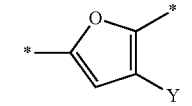
T-5

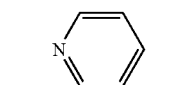
T-6

T-7

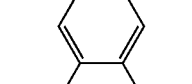
T-8

T-9

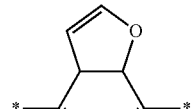
T-10

In one preferred embodiment in Formula (I) T is selected from $R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or $R^3$ and $R^4$ together form a substituent selected from the group consisting of:

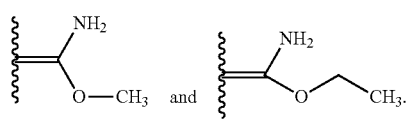

wherein $Z^A$=hydrogen, halogen, cyano, halomethyl ($CF_3$).

-continued
T-11 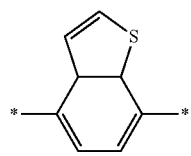
T-12 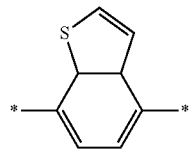
T-13 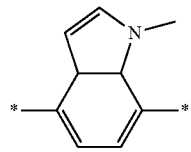
T-14 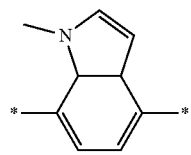
T-15 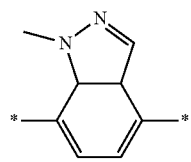
T-16 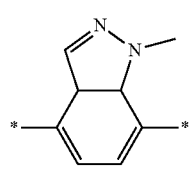
T-17 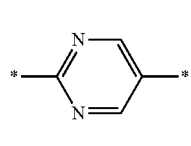
T-18 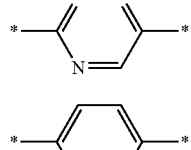
T-19 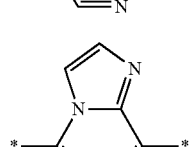
T-20 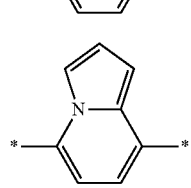
-continued
T-22 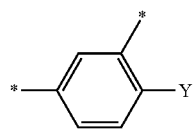
wherein in T-1, T-3 and T-4 the radical Y is hydrogen, halogen, methyl, halomethyl, ethyl, haloethyl.
In an preferred embodiment in Formula (I) Q is selected from
Q-1 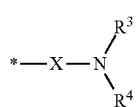
Q-2 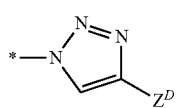
Q-3 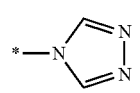
Q-4 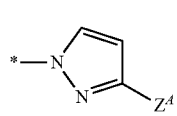
Q-5 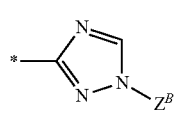
Q-6 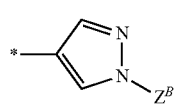
Q-7 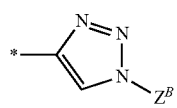
Q-8 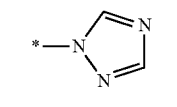
Q-9 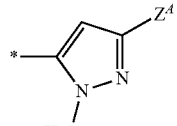
wherein $R^3$, $R^4$, X and $Z^A$ are as defined above.
$Z^B=$
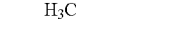
$Z^B$-1 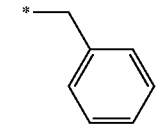

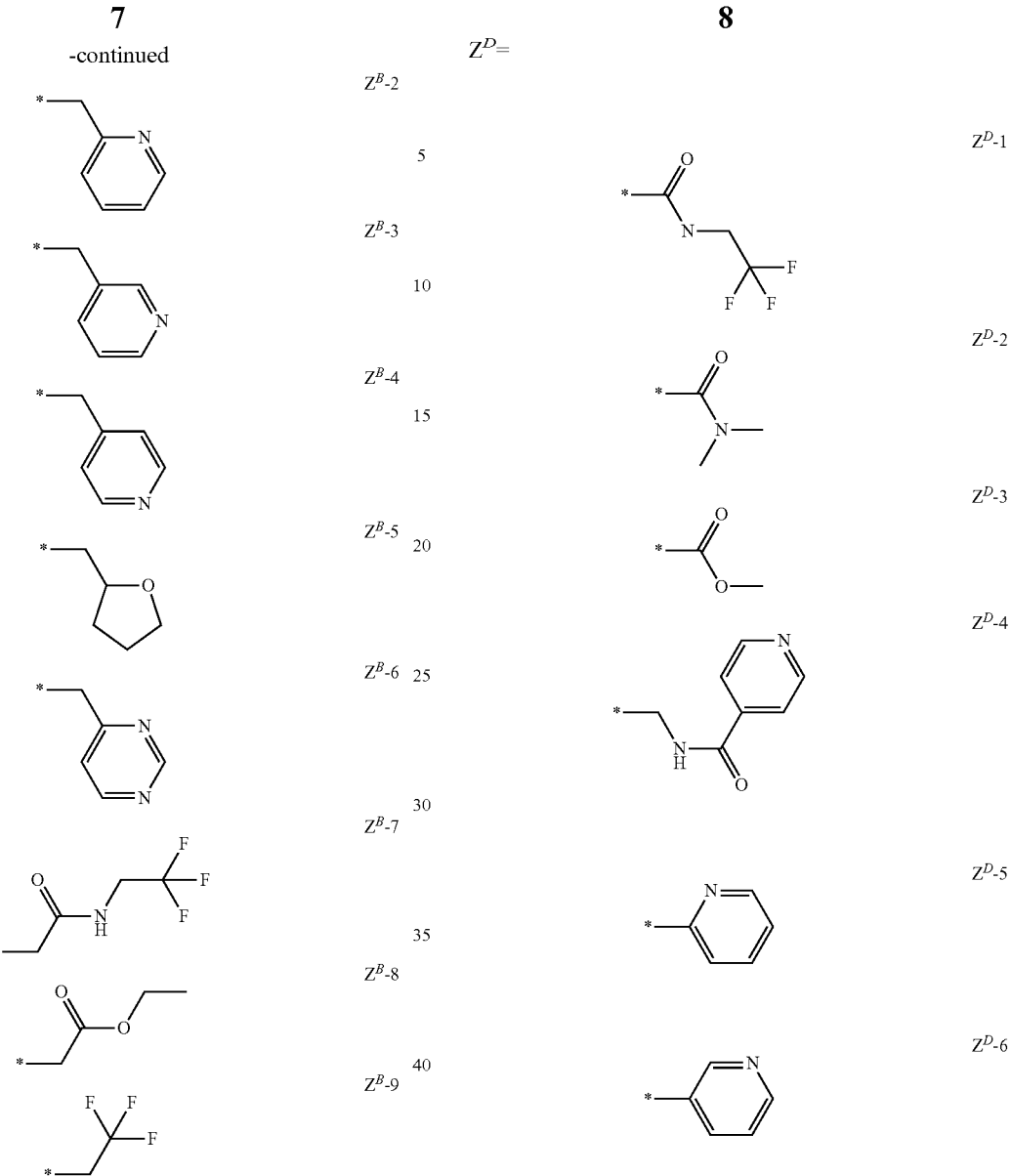

Preferred isoxazoline compounds of Formula (I) for use in the current invention are:

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-Cl, 5Cl | $CF_3$ | $CH_2C(O)NHCH_2CH_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CH_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CH_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | | T-2 | — | Q-7 | $Z^B$-7 | |
| 3-Cl, 5Cl | $CF_3$ | — | | T-2 | — | Q-5 | $Z^B$-7 | |
| 3-Cl, 5Cl | $CF_3$ | — | | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-Cl, 5Cl | $CF_3$ | $CH_2C(O)NHCH_2CH_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CH_3$ | H | T-3 | $CH_3$ | Q-1 | — | C(O) |
| 3-Cl, 4-Cl, | $CF_3$ | $CH_2C(O)NHCH_2CF_3$ | H | T-3 | $CH_3$ | Q-1 | — | C(O) |

-continued

| $(R^1)_n$ | $R^2$ | $R^3$ | $R^4$ | T | Y | Q | Z | X |
|---|---|---|---|---|---|---|---|---|
| 5-Cl | | | | | | | | |
| 3-Cl, 4-Cl, 5-Cl | $CF_3$ | $CH_2C(O)NHCH_2CH_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CH_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-Cl, 5-Cl | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CH_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CH_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-$CF_3$, 5-$CF_3$ | $CF_3$ | $CH_2C(O)NHCH_2CH_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CH_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |
| 3-Cl, 4-F, 5-Cl | $CF_3$ | $C(O)CH_3$ | H | T-22 | Cl | Q-1 | — | $CH_2$ |
| 3-Cl, 5-Cl | $CF_3$ | $CH_2C(O)NHCH_2CF_3$ | H | T-1 | $CH_3$ | Q-1 | — | C(O) |
| 3-Cl, 5-Cl | $CF_3$ | $CH_2C(O)NHCH_2CH_3$ | H | T-1 | $CH_3$ | Q-1 | — | C(O) |
| 3-Cl, 5-Cl | $CF_3$ | $R^3$-1 (Z) | H | T-1 | $CH_3$ | Q-1 | — | C(O) |
| 3-Cl, 5-Cl | $CF_3$ | $R^3$-1 (E) | H | T-1 | $CH_3$ | Q-1 | — | C(O) |

Especially preferred isoxazoline compounds for use in the current invention are

| $(R^1)_n$ | $R^2$ | $R^3$ | $R^4$ | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-Cl, 5Cl | $CF_3$ | $CH_2C(O)NHCH_2CC$ | H | T-3 | $CH_3$ | Q-1 | — | C(O) |
| 3-Cl, 5Cl | $CF_3$ | $CH_2C(O)NHCH_2CN$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH_2C(O)NHCH_2CF_3$ | H | T-3 | $CH_3$ | Q-1 | — | C(O) |
| 3-Cl, 5-Cl | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | $CH_3$ | T-20 | — | Q-1 | — | C(O) |
| 3-$CF_3$, 5-$CF_3$ | $CF_3$ | $CH_2C(O)NHCH_2CF_3$ | H | T-20 | — | Q-1 | — | C(O) |
| 3-$CF_3$, 5-$CF_3$ | $CF_3$ | $CH_2C(O)NHCH_2CF_3$ | H | T-21 | — | Q-1 | — | C(O) |
| 3-Cl, 5-Cl | $CF_3$ | $CH_2C(O)NHCH_2CF_3$ | H | T-21 | — | Q-1 | — | C(O) |
| 3-Cl, 5-Cl | $CF_3$ | $CH_2CH_2SCH_3$ | H | T-21 | — | Q-1 | — | C(O) |
| 3-Cl, 4-Cl, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH(CH_3)_2$ | H | T-22 | F | Q-1 | — | $CH_2$ |
| 3-Cl, 4-Cl, 5-Cl | $CF_3$ | C(O)-cyclo-propyl | H | T-22 | F | Q-1 | — | $CH_2$ |
| 3-Cl, 4-F, 5-Cl | $CF_3$ | $C(O)CH_3$ | H | T-22 | F | Q-1 | — | $CH_2$ |
| 3-Cl, 4-Cl, 5-Cl | $CF_3$ | $C(O)CH_2CH_3$ | H | T-22 | F | Q-1 | — | $CH_2$ |

-continued

| (R¹)ₙ | R² | R³ | R⁴ | T | Y | Q | Z | X |
|---|---|---|---|---|---|---|---|---|
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred isoxazoline compound for use in the current invention has the Formula (II),

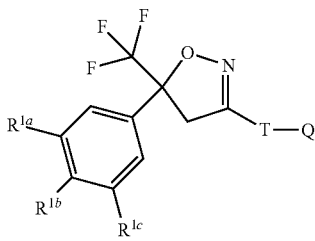

Formula II wherein
$R^{1a}$, $R^{1b}$, $R^{1c}$ are independently from each other hydrogen, Cl or CF₃, preferably $R^{1a}$ and $R^{1c}$ are Cl or CF₃ and $R^{1b}$ is hydrogen,
T is

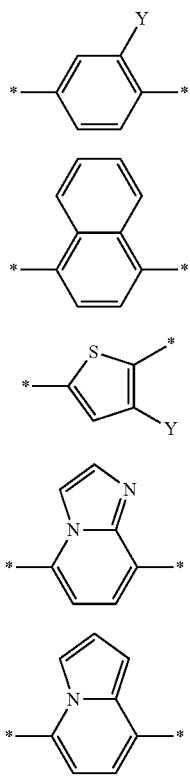

wherein
Y is methyl, bromine, Cl, F, CN or C(S)NH₂, and
Q is as described above.

In another preferred embodiment in Formula (II) R³ is H and R⁴ is —CH₂—C(O)—NH—CH₂—CF₃, —CH₂—C(O)—NH—CH₂—CH₃, —CH₂—CH₂—CF₃ or —CH₂—CF₃.

In a preferred embodiment the isoxazoline compound is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

In another embodiment the isoxazoline compound is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the isoxazoline compound is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another embodiment the isoxazoline compound is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaner) that was disclosed in WO2007/079162.

In another embodiment the isoxazoline compound is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068.

The current invention is directed to the use of such isoxazoline compounds or a salt or solvate thereof for inhibiting the development of juvenile stages of fleas originating from adult fleas that have been exposed to an isoxazound compound into adult stages.

In one embodiment the invention is directed to such use of the isoxazoline compounds wherein the development of juvenile stages of fleas to adult fleas in the environment is inhibited by systemic administration of sub-therapeutic amounts of said isoxazoline compound to the animal.

In one embodiment the invention is directed to such use of the isoxazoline compounds wherein the re-infestation of animals is inhibited by systemic administration of sub-therapeutic amounts of said isoxazoline compound to the animal. In a preferred embodiment such systemic administration is oral administration, in another embodiment topical administration, in another embodiment parenteral (injectable, especially subcutaneous) administration.

In one preferred embodiment the invention is directed to such use wherein such compound is fluralaner.

In one preferred embodiment the invention is directed to such use of the isoxazoline compounds wherein the blood plasma of the animal comprises isoxazoline compound concentrations between 1.5 and 25 ng/ml.

In one embodiment the invention is directed to such use of the isoxazoline compounds wherein the isoxazoline compound is administered to animals that are exposed to juvenile stages of fleas. In a preferred embodiment the animal is a dog or a cat.

In one embodiment the administration reduces the signs of allergic flea dermatitis.

In one embodiment the isoxazoline compound, especially fluralaner is used for preventing re-infestation of animals by fleas by administering to an flea infested animal a dose of an isoxazoline compound as defined in claim 1 sufficient to inhibit the development of the offspring of such fleas into adult stages.

In a preferred embodiment the dose of the isoxazoline compound is sufficient to reach blood plasma concentrations between 1.5 and 25 ng/ml. In one embodiment the isoxazoline compound, especially fluralaner is used for f preventing development of juvenile stages of fleas in an animal environment by administering to an flea infested animal a dose of an isoxazoline compound as defined in claim 1 sufficient to inhibit the development of juvenile stages of fleas into adult stages that originate from fleas, that have been exposed to such an isoxazoline compound.

The method of this invention comprises racemic mixtures, for example, equal amounts of the enantiomers. In addition, the method of this invention includes compounds that are enriched compared to the racemic mixture in an enantiomer of Formula 1. Also included are the essentially pure enantiomers of compounds of Formula 1.

When enantiomerically enriched, one enantiomer is present in greater amounts than the other, and the extent of enrichment can be defined by an expression of enantiomeric excess ("ee"), which is defined as (2x–1)·100%, where x is the mole fraction of the dominant enantiomer in the mixture (e.g., an ee of 20% corresponds to a 60:40 ratio of enantiomers). Preferably the compositions of Formula 1 have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. The method of this invention comprises racemic mixtures as well as enriched and essentially pure stereoconfigurations at these additional chiral centers. Compounds of Formula 1 can exist as one or more conformational isomers due to restricted rotation about the amide bond in Formula 1. The method of this invention comprises mixtures of conformational isomers. In addition, the method of this invention includes compounds that are enriched in one conformer relative to others. The reference to isoxazoline compound in this specification includes enantiomers, salts and solvates as well as N-oxides thereof that can be produced by conventional methods.

Isoxazoline compounds, such as fluralaner, have a potent inhibitory effect on flea reproduction that can be seen in both in vitro and in vivo experimental results. As shown in the example low concentrations of fluralaner (50.0 ng/mL and 25.0 ng/mL) achieved complete control of oviposition (100%), because fleas that survived 4-5 days of feeding at these concentrations did not produce any eggs (Table 2).

In the example high oviposition control rates were achieved even at sub-insecticidal isoxazoline concentrations including 99.6% (12.5 ng/mL) and 80.6% (6.25 ng/mL). It was shown that fluralaner does not affect the hatching of larvae, as hatch was observed in almost all flea groups that were able to lay eggs (Table 3). However, pupal development was strongly reduced (85.1% at 12.5 ng/mL, 88.7% at 6.25 ng/mL) indicating that fluralaner exposure has a potent larvicidal effect (Table 4). The same effect continued through to 100% control of adult emergence at 12.5 ng fluralaner/mL (Table 5).

The potent in vitro efficacy to control flea reproduction was supported by the in vivo study of treating dogs with oral fluralaner as compared to untreated control dogs in a simulated home environment. The home environment was created by allowing the dogs access to a carpeted bedding area and heavy flea-challenges during the month preceding the fluralaner treatment. This resulted in an environment with a thriving flea population including all developmental stages before treatment administration, leading to an increased flea burden on untreated-control dogs throughout the study duration. Following treatment, the flea populations were effectively controlled on the fluralaner (Bravecto™) treated dogs, with efficacy at, or near, 100% throughout the 12-week post-treatment period (Table 6).

Highly effective control of environmental flea populations has been recorded with topically applied insecticides that have contact activity against fleas, but is not reliably achieved with previously evaluated systemically administered insecticides.

"Prophylaxis" or "Prevention" means that a new infestation of the animal with parasites, especially fleas is prevented by reducing, or inhibiting the generation of offspring of the parasites e.g. by killing or inhibiting the development of juvenile stages or. Therefore a re-infestation of dogs by adult fleas originating from juvenile stages developed in the infested home environment (e.g. bedding, carpets) is prevented.

In general, the composition for use in the invention will contain a sub-insecticidal amount, this means an amount that is below the "effective" amount, that lead to plasma/serum concentrations that kills 100% of the adult fleas.

Sub-insecticidal (or sub-therapeutic) (plasma or serum) concentrations are concentrations that are below the level expected to provide a complete and instant adult flea killing effect (100% within 48 hours after administration of the isoxazoline compound). In one embodiment the sub-insecticidal amount (dosage) is 10% to 20% of the minimum effective amount to kill 100% of the adult fleas within 48 hours after administration of the isoxazoline compound. In another embodiment the sub-insecicidal (therapeutic) amount is between 20 and 50%, in another embodiment between 50 and 70% of the minimum effective amount.

Typically effective (dosage) amounts for isoxazoline compounds, are between 1 mg/kg bodyweight of the treated animal and 40 mg/kg bodyweight.

"Systemic administration" is an administration at a site remote from a site wherein at least a portion of the target parasites reside. With systemic administration, at least a portion of the isoxazoline compound reaches the target parasite via the animal recipient's bloodstream, other body fluids (lymph fluids), and/or tissues (e.g., skin or fat tissue). This is in contrast to "contact activity" were the surface of the parasite body is directly exposed to the isoxazoline compound. Typically, the parasite ingests the systemic administered isoxazoline along with the animal recipient's blood, other body fluids, and/or tissue. Systemic administration may be achieved in several forms, e.g. oral, parenteral or via topical administration wherein the isoxazoline compound is transdermally absorbed.

In some embodiments, the isoxazoline compound is systemically administered via an oral route in a unit dosage form, such as, for example, a soft or hard capsule, a pill, a powder, granules, a tablet (e.g., a chewable tablet), a paste, a solution, a suspension (aqueous or non-aqueous), an emulsion (oil-in-water or water-in-oil), an elixir, a syrup, a bolus, a drench, or via the animal recipient's feed or drinking water. Alternatively oral administration can be performed via the animal recipient's feed or drinking water e.g. it may be intimately dispersed in the animal recipient's regular feed, used as a top dressing, or in the form of pellets or liquid that is added to the finished feed.

One form of oral administration is a dosage form, e.g. a chewable composition, such as a chewable tablet. Examples of chewable tablets comprising isoxazoline compounds of formula (I) were described in WO2013/150052 and WO2013/150055. The composition of the chewable tablets that is disclosed in the examples of these documents is incorporated by reference. Alternative chewable tablets are described in WO2013/119442.

Oral veterinary compositions in the form of a "chewable tablet", sometimes referred to as "soft chewable compositions" or "soft chew", are usually convenient to administer to certain animals, particularly cats and dogs, preferably dogs, and may be used effectively to dose veterinary medicine to these animals.

A "Chewable tablet", "Soft chew" or "Soft chewable pharmaceutical product" is intended to mean a pharmaceutical unit dose that is solid at room temperature and that is after oral administration soft to chew by the animal and which is functionally chewy because the product has some plastic texture during the process of mastication in the mouth. Such soft chews have a softness that is similar to a cooked ground meat petty. The chewable tablet or soft chew comprises a carrier and other non-active ingredients.

The isoxazoline compound alternatively (or additionally) may be systemically administered topically using a transdermal formulation (i.e., a formulation that passes through the skin). Alternatively (or additionally), the composition may be systemically administered topically via the mucosa. The isoxazoline composition alternatively (or additionally) may be systemically administered parenterally, such as via intramuscular injection, intravenous injection, subcutaneous injection, implant (e.g., subcutaneous implant), infusion, bolus, etc.

The animals may receive a pharmaceutical composition comprising an isoxazoline compound as defined earlier every 1, 2, 3, 4, 5 or 6 months or receives a yearly, half-yearly, quarterly, bimonthly, monthly, weekly or daily dosage. Preferred is an administration of a pharmaceutical composition according to the current invention every 3 months or quarterly.

In general the isoxazoline compound can be administered to all species of animals that have parasite infestation.

The recipient of the product may be a livestock animal, e.g. sheep, cattle, pig, goat or poultry; a laboratory test animal, e.g. guinea pig, rat or mouse; or a companion animal, e.g. dog, cat, rabbit, ferret or horse. Especially preferred is the use in companion animals, e.g. dogs, cats or ferrets, preferably dogs or cats, especially dogs.

An "infestation" refers to the presence of parasites in numbers that pose a risk of nuisance or harm to humans or animals. The presence can be in the environment (e.g., in animal bedding), on the skin or fur of an animal, etc.

Unless otherwise stated, when the infestation is within an animal (e.g., in the blood or other internal tissues), the term infestation is intended to be synonymous with the term, "infection," as that term is generally understood in the art.

For many animal recipients, the isoxazoline amounts that are administered systemically are chosen to maintain an isoxazoline plasma or serum level (especially in case the isoxazoline compound is fluralaner) of about 1.5 to 50 ng/ml, 2 to 30 ng/ml, 3 ng/ml to 25 ng/ml 2 to 20 ng/ml, 3 to 15 ng/ml. Preferred is a serum/plasma level of isoxazolines, especially fluralaner of between 5 to 12.5 ng/ml or 1.56, to 50 ng/ml), especially 50 ng/ml, 25 ng/ml, 12.5 ng/ml, 6.25 ng/ml, 3.13 ng/ml, or 1.56 ng/ml.

Alternatively the isoxazoline compounds as described above can be administered to animals to prevent the maturation of juvenile stages of other ectoparasites such as:

A. Biting insects. These include, for example, migrating diperous larvae, such as, for example, *Hypoderma* sp. in cattle, *Gastrophilus* in horses, and *Cuterebra* sp. in rodents; biting flies, such as, for example, bloodsucking adult flies (e.g., the horn fly (*Haematobia irritans*), horse flies (e.g. *Tabanus* spp.), stable flies (e.g. *Stomoxys calcitrans*), black flies (e.g. *Simulium* spp.), deer flies (e.g. *Chrysops* spp.), louse flies (e.g. *Melophagus ovinus*), tsetse flies (e.g. *Glossina* spp.); parasitic fly maggots, such as, for example, bot flies (e.g. *Oestrus ovis* and *Cuterebra* spp.), the blow flies (e.g. *Phaenicia* spp.), screwworms (e.g. *Cochliomyia hominivorax*), cattle grubs (e.g. *Hypoderma* spp.), and fleeceworms; and mosquitoes, such as, for example, *Culex* spp., *Anopheles* spp., and *Aedes* spp.

B. Mites. These include:

i. *Mesostigmata* spp., such as mesostigmatids, which include chicken mites (e.g. *Dermanyssus gallinae*).

ii. *Astigmata* spp., such as itch or scab mites, which include Sarcoptidae spp. (e.g., *Sarcoptes scabiei*); and mange mites, which include Psoroptidae spp. (e.g., *Chorioptes bovis* and *Psoroptes ovis*).

iii. *Prostigmata* spp., such as chiggers, which include Trombiculidae spp. (e.g., North American chiggers, *Trombicula alfreddugesi*).

iv. *Demodex*.

C. Ticks. These include, for example, soft-bodied ticks, such as Argasidae spp. (e.g., *Argas* spp. and *Ornithodoros* spp.); and hard-bodied ticks, such as Ixodidae spp. (e.g., *Ixodes ricinus*, *Rhipicephalus sanguineus*, *Haemaphysalis* spp, *Dermacentor reticulates*, *Dermacentor variabilis*, *Amblyomma americanum*, and *Rhipicephalus* (*Boophilus*) spp.).

D. Lice. These include, for example, chewing lice, such as *Menopon* spp. and *Bovicola* spp.; and sucking lice, such as *Haematopinus* spp., *Linognathus* spp., and *Solenopotes* spp.

E. Fleas. These include, for example, Ctenocephalides spp., such as dog fleas (*Ctenocephalides canis*) and cat fleas (*Ctenocephalides felis*); *Xenopsylla* spp., such as oriental rat fleas (*Xenopsylla cheopis*); *Pulex* spp., such as human fleas (*Pulex irritans*); hedgehog fleas (*Archaeopsylla erinacei*); and bird fleas (*Ceratophyllus gallinae*).

F. True bugs. These include, for example, Cimicidae or the common bed bug (*Cimex lectularius*); and Triatominae spp., such as triatomid bugs (also known as kissing bugs) (e.g., *Rhodnius prolixus* and *Triatoma* spp.).

The current invention furthermore provides a method of preventing re-infestation of animals by fleas by administering to an flea infested animal a dose of an isoxazoline compound as defined in claim 1 sufficient to inhibit the development of juvenile stages of fleas into adult stages that originate from adult fleas (i.e. their offspring) that have been exposed to such an isoxazoline compound.

In such method the isoxazoline compound is preferably fluralaner.

In such method the dose is sufficient to reach blood plasma concentrations of the isoxazoline compound between 1.5 and 25 ng/ml.

In such method the animal is a dog or a cat.

In such method the systemic administration is an oral administration.

Alternatively, in such method the systemic administration is a topical administration.

Alternatively, in such method the systemic administration is a parenteral administration The current invention further provides a method of preventing development of juvenile stages of fleas in an animal environment by administering to an flea infested animal a dose of an isoxazoline compound as defined in claim 1 sufficient to inhibit the development of juvenile stages of fleas into adult stages that originate from adult fleas (i.e. their offspring) that have been exposed to such an isoxazoline compound.

In such method the isoxazoline compound is preferably fluralaner.

In such method the dose is sufficient to reach blood plasma concentrations of the isoxazoline compound between 1.5 and 25 ng/ml.

In such method the animal is a dog or a cat.

In such method the systemic administration is an oral administration. Alternatively, in such method the systemic administration is a topical administration. Alternatively, in such method the systemic administration is a parenteral administration

EXAMPLES

Example 1 In Vitro Membrane Feeding Exposure to Assess Flea Reproduction

A membrane feeding method [Wade S E, Georgi J R. Survival and reproduction of artificially fed cat fleas, *Ctenocephalides felis* Bouché (Siphonaptera: Pulicidae). J Med Entomol 1988, 25: 186-190.] was modified to assess the impact of fluralaner exposure on flea reproduction. Defibrinated sheep blood was prepared in a series of dilutions with fluralaner to obtain concentrations between 50.0 and 0.09 ng/mL. These test solutions were prepared twice and each preparation was tested in duplicate resulting in a total of 4 replicates per concentration, along with a fluralaner negative solvent control (a solvent concentration equivalent to that of the highest concentrated fluralaner test solution) and an untreated control.

Unfed adult fleas (*C. felis*; 20 males and 20 females) were placed into a plastic unit that was then closed with a gauze lid. A grid inside the plastic unit divided the unit into 2 chambers, an upper chamber for flea feeding and a lower chamber for egg collection [8]. Test or control blood preparations (2 ml) were placed in an artificial membrane closed glass tube that was then placed on the plastic unit as the food source. Feeding units were incubated (38° C. and 60% RH) for 10 days. Test and negative control blood preparations were freshly prepared and exchanged (on days 1, 3, 5, and 8) to permit continuous flea feeding. Fleas were transferred into fresh plastic units on Days 5 and 8 to facilitate egg collection. Collected eggs were mixed with flea nourishment medium and incubated (28° C. and 80% RH) in darkness for 22 (±3) days to enable flea development. Parameters recorded were flea survival, oviposition control, egg hatchability, pupa control, flea-emergence control and reproduction inhibition.

Results

Impact on Flea Reproduction after In Vitro Membrane-Feeding Exposure

Feeding exposure to concentrations of 50 ng fluralaner/mL resulted in a flea survival of 78.1% (day 2), 20.0% (day 3), 8.7% (day 4) and 1.2% (day 5). At 25 ng/mL flea survival rates were 90.6% (day 2), 67.5% (day 3), 31.9% (day 4) and 11.3% (day 5). The flea survival rates increased at lower concentrations (Table 1). Concentrations of 50 and 25 ng fluralaner/mL achieved complete control of oviposition (100%), because fleas that survived 4 to 5 days of feeding at these concentrations did not produce any eggs. At lower concentrations of 12.5 and 6.25 ng fluralaner/mL, the oviposition was controlled by 99.6% and 80.6%, respectively (Table 2). Fluralaner did not affect the hatching of larvae, as hatch was observed in almost all flea groups that were able to lay eggs (Table 3). The pupal development was strongly reduced (85.1% at 12.5 ng fluralaner/mL, 88.7% at 6.25 ng fluralaner/mL) indicating that fluralaner exposure has a potent larvicidal effect (Table 4). The same effect continued through to 100% control of adult emergence at 12.5 ng fluralaner/mL (Table 5).

TABLE 1

Flea survival after feeding on blood containing fluralaner at sub-insecticidal concentrations.

| Fluralaner | Flea Survival (%) Exposure Day [a] | | | | | | |
|---|---|---|---|---|---|---|---|
| (ng/mL) | 2 | 3 | 4 | 5 | 8 | 9 | 10 |
| 50.0 | 78.1 | 20.0 | 8.7 | 1.2 | 0 | 0 | 0 |
| 25.0 | 90.6 | 67.5 | 31.9 | 11.3 | 0 | 0 | 0 |
| 12.5 | 100 | 100 | 67.5 | 38.9 | 21.7 | 17.9 | 12.3 |
| 6.25 | 100 | 100 | 97.5 | 92.8 | 85.0 | 73.1 | 69.7 |
| 3.13 | 100 | 100 | 98.7 | 97.8 | 83.1 | 79.5 | 78.8 |
| 1.56 | 100 | 100 | 99.4 | 99.1 | 93.9 | 92.9 | 90.3 |
| 0.78 | 100 | 100 | 100 | 100 | 100 | 100 | 100 |
| 0.39 | 100 | 100 | 100 | 100 | 100 | 100 | 98.7 |
| 0.19 | 100 | 100 | 100 | 100 | 100 | 100 | 100 |
| 0.09 | 100 | 100 | 100 | 100 | 100 | 100 | 100 |

[a] No flea counts were performed on exposure days 6 and 7.

TABLE 2

Flea oviposition control after feeding on blood containing fluralaner at sub-insecticidal concentrations.

| Fluralaner | Oviposition Control (%) Exposure Day [a] | | | | | | |
|---|---|---|---|---|---|---|---|
| (ng/mL) | 3 | 4 | 5 | 8 | 9 | 10 | Mean [b] |
| 50.0 | 100 | 100 | 100 | NA. | NA. | NA. | 100 |
| 25.0 | 100 | 100 | 100 | NA. | NA. | NA. | 100 |
| 12.5 | 99.6 | 100 | 100 | 98.9 | 99.1 | 100 | 99.6 |
| 6.25 | 82.6 | 85.9 | 81.3 | 79.9 | 67.5 | 86.4 | 80.6 |
| 3.13 | 32.0 | 35.7 | 43.1 | 70.5 | 59.9 | 62.0 | 50.5 |
| 1.56 | 0 | 0 | 17.3 | 49.8 | 30.1 | 29.2 | 21.1 |
| 0.78 | 8.7 | 3.0 | 13.8 | 12.5 | 0 | 18.5 | 9.4 |
| 0.39 | 6.72 | 22.8 | 23.2 | 23.8 | 0 | 20.3 | 16.1 |
| 0.19 | 0 | 5.1 | 21.0 | 15.1 | 0 | 13.9 | 9.2 |
| 0.09 | 0 | 11.3 | 10.9 | 16.7 | 0.3 | 8.1 | 7.9 |

[a] No egg counts were performed on exposure days 6 and 7.
[b] Arithmetic mean
NA.: not applicable because all fleas were killed (Table 1)

TABLE 3

Flea larvae emergence from eggs of parent fleas fed on blood containing fluralaner at sub-insecticidal concentrations.

| Fluralaner (ng/mL) | Larval Emergence Exposure Day [a] | | | | | |
|---|---|---|---|---|---|---|
| | 3 | 4 | 5 | 8 | 9 | 10 |
| 50.0 | NA | NA | NA | NA | NA | NA |
| 25.0 | NA | NA | NA | NA | NA | NA |
| 12.5 | no | NA | NA | yes | yes | NA |
| 6.25 | yes | yes | yes | yes | yes | yes |
| 3.13 | yes | yes | yes | yes | yes | yes |
| 1.56 | yes | yes | yes | yes | yes | yes |
| 0.78 | yes | yes | yes | yes | yes | yes |
| 0.39 | yes | yes | yes | yes | yes | yes |
| 0.19 | yes | yes | yes | yes | yes | yes |
| 0.09 | yes | yes | yes | yes | yes | yes |

[a] No assessment of larval emergence was performed on exposure days 6 and 7.
NA: not applicable because fleas were either killed or did not lay eggs (Table 1 and Table 2)

TABLE 4

Pupal development control from eggs of parent fleas fed on blood containing fluralaner at sub-insecticidal concentrations.

| Fluralaner (ng/mL) | Pupal Development Control (%) Exposure Day [a] | | | | | | |
|---|---|---|---|---|---|---|---|
| | 3 | 4 | 5 | 8 | 9 | 10 | Mean [b] |
| 50.0 | NA | NA | NA | NA | NA | NA | NA |
| 25.0 | NA | NA | NA | NA | NA | NA | NA |
| 12.5 | 100 | NA | NA | 55.2 | 100 | NA | 85.1 |
| 6.25 | 90.2 | 92.4 | 87.3 | 86.4 | 89.9 | 86.0 | 88.7 |
| 3.13 | 66.3 | 68.9 | 61.7 | 70.3 | 62.1 | 57.4 | 64.5 |
| 1.56 | 35.3 | 36.3 | 34.6 | 35.5 | 41.6 | 27.2 | 35.1 |
| 0.78 | 7.5 | 11.4 | 16.7 | 10.8 | 11.9 | 14.5 | 12.1 |
| 0.39 | 9.8 | 0 | 1.5 | 3.3 | 6.3 | 0.8 | 3.6 |
| 0.19 | 8.8 | 0.2 | 6.8 | 0 | 2.7 | 0 | 3.1 |
| 0.09 | 9.1 | 4.5 | 1.4 | 0 | 5.9 | 2.9 | 4.0 |

[a] No pupal counts were performed on exposure days 6 and 7.
[b] Arithmetic mean
NA: not applicable because fleas were either killed or did not lay eggs (Table 1 and Table 2)

TABLE 5

Adult flea emergence control after parent fleas fed on blood containing fluralaner at sub-insecticidal concentrations.

| Fluralaner (ng/mL) | Adult Flea Emergence Control (%) Exposure Day [a] | | | | | | |
|---|---|---|---|---|---|---|---|
| | 3 | 4 | 5 | 8 | 9 | 10 | Mean [b] |
| 50.0 | NA | NA | NA | NA | NA | NA | NA |
| 25.0 | NA | NA | NA | NA | NA | NA | NA |
| 12.5 | NA | NA | NA | 100 | NA | NA | 100 |
| 6.25 | 29.2 | 0 | 0 | 9.2 | 30.8 | 0 | 11.5 |
| 3.13 | 4.4 | 11.9 | 3.2 | 8.6 | 7.5 | 0 | 5.9 |
| 1.56 | 0 | 0 | 0 | 10.2 | 0 | 0 | 1.7 |
| 0.78 | 3.8 | 0 | 0 | 3.1 | 1.8 | 0 | 1.5 |
| 0.39 | 0 | 0 | 0 | 1.6 | 5.2 | 0 | 1.1 |
| 0.19 | 4.6 | 0 | 1.3 | 0.8 | 6.7 | 0 | 2.2 |
| 0.09 | 1.1 | 0.5 | 0 | 0 | 0 | 0 | 0.3 |

[a] No adult flea counts were performed on exposure days 6 and 7
[b] Arithmetic mean
NA: not applicable because fleas were either killed or did not lay eggs (Table 1, Table 2, and Table 4)

Example 2 In Vivo Study in Dogs to Assess Flea Control Efficacy in a Simulated Home Environment Study Procedures Twenty healthy male and female mixed-breed dogs ≥12 weeks old were housed in individual pens. Ten dogs per group were randomly assigned to receive either a fluralaner chewable tablet (Bravecto™) or no treatment. Each pen contained the bottom half of a dog carrier lined with carpet as bedding. Before treatment, each dog was infested twice (28 and 21 days pretreatment) with 100 adult, unfed *C. felis* to establish a flea population prior to treatment on each dog. Flea media was added to the carpet 4 weeks before the treatment date and weekly thereafter for the remainder of the study to encourage development of an active, developing population of juvenile flea stages in each pen. On the treatment day, dogs in the treated group received fluralaner at a dose close to 25 mg/kg body weight by oral administration. The chewable tablet(s) were administered by placement in the back of the oral cavity over the tongue to initiate swallowing. Dogs in the negative control group remained untreated.

Flea counts were performed on all dogs 1 day before treatment, 1 day after treatment and then every 7 days until completion of the study 84 days later. All live fleas recovered were held and re-infested on the dog after the comb count was completed. Each dog was also infested with 50 newly emerged unfed adult fleas on days 22, 50 and 78 to simulate natural infestation post-treatment.

Statistical Analysis

The individual dog was the experimental unit and data from each flea count time point were analyzed separately. Flea count data were transformed $[Y=\log_e(x+1)]$ and analyzed by a mixed linear model including treatment as the fixed effect and block as the random effect. Kenward-Rogers adjustment was used to determine the denominator degree of freedom. A two-tailed test was used within the mixed linear model for the comparison between treatment groups and statistical significance was declared when $P \leq 0.05$. SAS version 9.3 was the primary software used for analysis.

Efficacy was calculated using arithmetic and geometric means with Abbott's formula: Efficacy (%)=100×($M_C$−$M_T$)/$M_C$, where $M_C$ was the arithmetic or geometric mean number of total adult live fleas on untreated dogs and $M_T$ the arithmetic or geometric mean number of total adult live fleas on treated dogs.

Results

No adverse events were observed in any fluralaner (Bravecto™) treated dog following administration. Mean flea counts (arithmetic/geometric) on untreated-control dogs were 52.3/26.4 fleas before the day of treatment (day −1) and in the range of 5.1/1.8 to 57.1/40.6 fleas following treatment. Mean flea counts (arithmetic/geometric) on fluralaner-treated dogs were 35.0/14.1 fleas before treatment, 0/0 fleas on days 1, 7, 14, 21, 28, 35, 42, 63, 77 and 84, and 0.1/0.1 fleas on days 49, 56, and 70 after treatment. Compared to control, these counts were significantly different ($P \leq 0.021$) on all post-treatment count days. Calculated efficacy results were either 100% or very close to 100% at all post-treatment time points (Table 6).

TABLE 6

Flea-control efficacy on treated dogs (25 mg fluranaler/kg body weight) compared with untreated dogs in a simulated home environment.

| Day post treatment | Mean flea numbers (arithmetic/geometric) Control group | Mean flea numbers (arithmetic/geometric) Treated group | Efficacy[a] (%) | P-value |
|---|---|---|---|---|
| −1 | 52.3/26.4 | 35.0/14.1 | N/A | N/A |
| 1 | 12.8/6.0 | 0/0 | 100/100 | 0.001 |
| 7 | 5.1/1.8 | 0/0 | 100/100 | 0.021 |
| 14 | 7.1/2.7 | 0/0 | 100/100 | 0.012 |
| 21 | 16.5/4.1 | 0/0 | 100/100 | 0.011 |
| 28 | 53.2/24.8 | 0/0 | 100/100 | 0.000 |
| 35 | 44.1/15.7 | 0/0 | 100/100 | 0.000 |
| 42 | 42.6/10.8 | 0/0 | 100/100 | 0.002 |
| 49 | 48.7/20.6 | 0.1/0.1 | 99.8/99.7 | 0.000 |
| 56 | 57.1/40.6 | 0.1/0.1 | 99.8/99.8 | 0.000 |
| 63 | 42.3/25.6 | 0/0 | 100/100 | 0.000 |
| 70 | 30.0/16.2 | 0.1/0.1 | 99.7/99.6 | 0.000 |
| 77 | 21.9/12.3 | 0/0 | 100/100 | 0.000 |
| 84 | 40.7/33.2 | 0/0 | 100/100 | 0.000 |

[a]Efficacy calculated from arithmetic/geometric mean flea counts.
NA: not applicable

The invention claimed is:

1. A Method of preventing re-infestation of animals by fleas comprising administering to an flea infested animal a sub-insecticidal dose of an isoxazoline compound of formula (I)

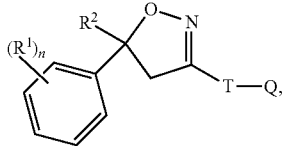

Formula (I)

wherein
$R^1$=halogen, $CF_3$, $OCF_3$, CN,
n=integer from 0 to 3
$R^2$=$C_1$-$C_3$-haloalkyl,
T=5- or 6-membered ring, which is optionally substituted by one or more radicals Y,
Y=methyl, halomethyl, halogen, CN, $NO_2$, $NH_2$—C=S, or two adjacent radicals Y form together a chain;
Q=X—$NR^3R^4$ or a 5-membered N-heteroaryl ring, which is optionally substituted by one or more radicals;
X=$CH_2$, CH($CH_3$), CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

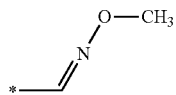 R³-1

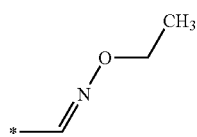 R³-2

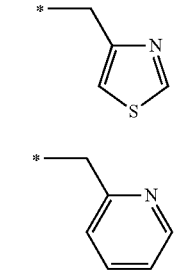 R³-3

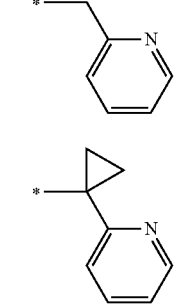 R³-4

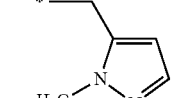 R³-5

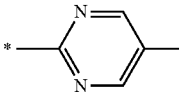 R³-6

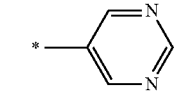 R³-7

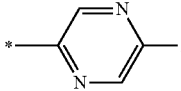 R³-8

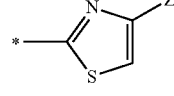 R³-9

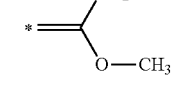 R³-10

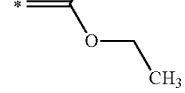 R³-11

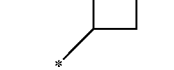 R³-12

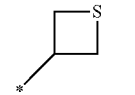 R³-13

-continued

R³-14
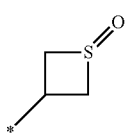

R³-15
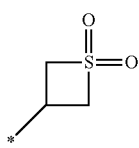

wherein $Z^4$=hydrogen, halogen, cyano, halomethyl, $R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl, Or $R^3$ and $R^4$ together form a substituent selected from the group consisting of:

1. 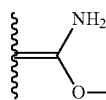 and 2. 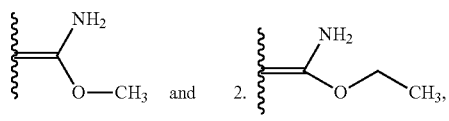

sufficient to inhibit the development of the offspring of such fleas into adult stages and to reach blood plasma concentrations between 1.5 and 25 ng/ml, wherein the administration is topical administration or parenteral administration.

2. The method of claim 1, wherein the administration is parenteral administration.

3. The method of claim 1, wherein n is 1, 2 or 3.

4. The method of claim 1, wherein $R^2$ is $CF_3$ or $CF_2Cl$.

5. The method of claim 1, wherein two adjacent radicals Y form together a three or four membered chain.

6. The method according to claim 2 wherein the isoxazoline compound is fluralaner.

7. The method according to claim 2, wherein the animal is a dog or a cat.

8. The method of claim 1, wherein the administration is topical administration.

9. The method according to claim 8 wherein the isoxazoline compound is fluralaner.

10. The method of claim 8, wherein the animal is a dog or a cat.

11. The method of claim 1, wherein $Z^4$ is $CF_3$.

* * * * *